United States Patent
Nomaru et al.

(10) Patent No.: US 10,207,369 B2
(45) Date of Patent: Feb. 19, 2019

(54) METHOD FOR FORMING A LASER PROCESSED HOLE

(71) Applicant: DISCO CORPORATION, Tokyo (JP)

(72) Inventors: Keiji Nomaru, Tokyo (JP); Hiroshi Morikazu, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days.

(21) Appl. No.: 15/080,958

(22) Filed: Mar. 25, 2016

(65) Prior Publication Data

US 2016/0199940 A1 Jul. 14, 2016

Related U.S. Application Data

(62) Division of application No. 13/736,198, filed on Jan. 8, 2013, now abandoned.

(30) Foreign Application Priority Data

Jan. 27, 2012 (JP) .................................. 2012-015806

(51) Int. Cl.
*B23K 26/03* (2006.01)
*B23K 26/38* (2014.01)
(Continued)

(52) U.S. Cl.
CPC ............ *B23K 26/384* (2015.10); *B23K 26/03* (2013.01); *B23K 26/0622* (2015.10);
(Continued)

(58) Field of Classification Search
CPC .. B23K 26/03; B23K 26/0622; B23K 26/385; B23K 26/386; B23K 26/40;
(Continued)

(56) References Cited

U.S. PATENT DOCUMENTS 6,215,094 B1 * 4/2001 Dausinger ............ B23K 26/032
219/121.62
6,414,263 B1 * 7/2002 Uchida .................. B23K 26/03
219/121.71
(Continued)

FOREIGN PATENT DOCUMENTS

JP          08-192283        7/1996
JP          2003-163323      6/2003
(Continued)

OTHER PUBLICATIONS

Office Action dated Sep. 4, 2015, issued in U.S. Appl. No. 13/736,198, filed Jan. 8, 2013.
(Continued)

*Primary Examiner* — Dana Ross
*Assistant Examiner* — Lawrence Samuels
(74) *Attorney, Agent, or Firm* — Greer Burns & Crain, Ltd.

(57) ABSTRACT

A method for forming a laser processed hole in a workpiece configured by bonding a transparent first member formed of a first material and a second member formed of a second material. The method includes holding the workpiece by a chuck table with a side of the first member directed upward; applying a pulsed laser beam to the workpiece from the upward side of the first member; detecting a wavelength of plasma light generated by applying the pulsed laser beam to the workpiece; and controlling the laser beam according to a detection signal from the plasma light. The plasma is detected by: passing only the wavelength of plasma light generated from the first material, and detecting the plasma light generated from the first material and outputting a light intensity signal based on the detection. The processed hole extends entirely through the first member without melting the second member.

1 Claim, 11 Drawing Sheets

(51) Int. Cl.
*B23K 26/384* (2014.01)
*B23K 26/0622* (2014.01)
*H01L 21/768* (2006.01)
*G01N 21/71* (2006.01)
*B23K 26/40* (2014.01)
*B23K 26/382* (2014.01)
*B23K 103/16* (2006.01)

(52) U.S. Cl.
CPC ............ *B23K 26/389* (2015.10); *B23K 26/40* (2013.01); *G01N 21/718* (2013.01); *H01L 21/76898* (2013.01); *B23K 2103/172* (2018.08)

(58) Field of Classification Search
CPC .............. B23K 26/409; B23K 26/0853; B23K 26/032; G01N 21/718; G01N 27/00; H01L 21/76898
USPC ... 219/121.6–121.61, 121.64, 121.7, 121.71, 219/121.62, 121.68, 121.73, 121.83
See application file for complete search history.

(56) References Cited

U.S. PATENT DOCUMENTS

| | | | |
|---|---|---|---|
| 9,061,369 B2* | 6/2015 | Yoo ................ | B23K 26/032 |
| 2008/0070327 A1* | 3/2008 | Ogasawara ....... | H01J 37/32935 |
| | | | 438/9 |
| 2009/0127233 A1 | 5/2009 | Asano et al. | |
| 2011/0100967 A1* | 5/2011 | Yoo ................ | B23K 26/032 |
| | | | 219/121.73 |

FOREIGN PATENT DOCUMENTS

| | | |
|---|---|---|
| JP | 2007-067082 | 3/2007 |
| JP | 2007-157900 | 6/2007 |
| JP | 2009-125756 | 6/2009 |

OTHER PUBLICATIONS

Office Action dated Dec. 30, 2015, issued in U.S. Appl. No. 13/736,198, filed Jan. 8, 2013.

\* cited by examiner

METHOD FOR FORMING A LASER PROCESSED HOLE

This is a divisional of application Ser. No. 13/736,198, filed Jan. 8, 2013.

BACKGROUND OF THE INVENTION

Field of the Invention

The present invention relates to a laser processing apparatus for forming a laser processed hole in a workpiece configured by bonding a first member formed of a first material and a second member formed of a second material, the laser processed hole extending from the first member to the second member.

Description of the Related Art

In a semiconductor device fabrication process, a plurality of crossing division lines called streets are formed on the front side of a substantially disk-shaped semiconductor wafer to thereby partition a plurality of regions where devices such as ICs and LSIs are respectively formed. The semiconductor wafer is cut along the streets to thereby divide the regions where the devices are formed from each other, thus obtaining individual semiconductor chips. For the purposes of achieving smaller sizes and higher functionality of equipment, a module structure having a following configuration is in practical use. This module structure is such that a plurality of devices is stacked and bonding pads provided on each device are connected to each other. In this module structure, through holes (via holes) are formed in a semiconductor wafer at positions corresponding to the bonding pads, and a conductive material such as aluminum is embedded in each via hole so as to be connected to the corresponding bonding pad (see Japanese Patent Laid-open No. 2003-163323, for example).

Each via hole in the semiconductor wafer mentioned above is formed by using a drill. However, the diameter of each via hole in the semiconductor wafer is as small as 90 to 300 μm, so that the formation of each via hole by using a drill causes a reduction in productivity. To solve this problem, there has been proposed a hole forming method for a wafer composed of a substrate and a plurality of devices formed on the front side of the substrate, a plurality of bonding pads being formed on each device, in which a pulsed laser beam is applied to the substrate from the back side thereof to thereby efficiently form a plurality of via holes respectively reaching the plural bonding pads (see Japanese Patent Laid-open No. 2007-67082, for example).

A wavelength of the pulsed laser beam is selected so as to have low absorptivity to a metal forming the bonding pads and have high absorptivity to a material forming the substrate, such as silicon and lithium tantalate. However, in applying the pulsed laser beam to the substrate from the back side thereof to thereby form the via holes respectively reaching the bonding pads, it is difficult to stop the application of the pulsed laser beam at the time each via hole formed in the substrate has reached the corresponding bonding pad, causing a problem that the bonding pads may be melted to be perforated by the pulsed laser beam. To solve this problem in the hole forming method for the wafer disclosed in Japanese Patent Laid-open No. 2007-67082, there has been proposed a laser processing apparatus such that a laser beam is applied to a material to generate a plasma from the material, and a spectrum caused by this plasma and inherent in the material is detected to thereby determine that the laser beam has reached each bonding pad formed of metal (see Japanese Patent Laid-open No. 2009-125756, for example).

SUMMARY OF THE INVENTION

Each bonding pad formed of metal is located at the bottom of a fine hole formed by applying a laser beam. Accordingly, even when the laser beam is applied to each bonding pad, it is difficult to capture a moment of proper generation of the plasma from the metal forming each bonding pad and then stop the application of the laser beam, causing a problem that each bonding pad may be melted to be perforated.

It is therefore an object of the present invention to provide a laser processing apparatus which can efficiently form a laser processed hole in a workpiece configured by bonding a first member formed of a first material and a second member formed of a second material, the laser processed hole extending from the first member to the second member.

In accordance with an aspect of the present invention, there is provided a laser processing apparatus for forming a laser processed hole in a workpiece configured by bonding a first member formed of a first material and a second member formed of a second material, the laser processed hole extending from the first member to the second member, the laser processing apparatus including workpiece holding means for holding the workpiece; laser beam applying means for applying a pulsed laser beam to the workpiece held by the workpiece holding means; plasma detecting means for detecting a wavelength of plasma light generated by applying the pulsed laser beam from the laser beam applying means to the workpiece; and control means for controlling the laser beam applying means according to a detection signal from the plasma detecting means. The plasma detecting means includes a bandpass filter for passing only the wavelength of plasma light generated from the first material and a photodetector for detecting the light passed through the bandpass filter and outputting a light intensity signal to the control means. The control means controls the laser beam applying means so that, when the laser beam applying means is operated to apply the pulsed laser beam to the workpiece to thereby form the laser processed hole extending from the first member to the second member, the amplitude of a light intensity is detected according to the light intensity signal output from the photodetector, and the application of the pulsed laser beam is stopped after the amplitude of the light intensity is decreased to a predetermined value and a predetermined number of shots of the pulsed laser beam is next applied.

In the laser processing apparatus according to the present invention, the plasma detecting means for detecting the wavelength of plasma light generated by applying the pulsed laser beam from the laser beam applying means to the workpiece includes the bandpass filter for passing only the wavelength of plasma light generated from the first material and the photodetector for detecting the light passed through the bandpass filter and outputting the light intensity signal to the control means. The control means for controlling the laser beam applying means according to the detection signal from the plasma detecting means controls the laser beam applying means so that, when the laser beam applying means is operated to apply the pulsed laser beam to the workpiece to thereby form the laser processed hole extending from the first member to the second member, the amplitude of the light intensity is detected according to the light intensity signal output from the photodetector, and the application of the pulsed laser beam is stopped after the amplitude of the light intensity is decreased to the predetermined value and the predetermined number of shots of the pulsed laser beam is next applied. With this configuration, the application of the pulsed laser beam is stopped at the time the laser processed hole (fine hole) formed in the first member by applying the pulsed laser beam thereto has reached the second member, so that there is no possibility that the second member may be melted.

Accordingly, in the case that the workpiece is a wafer including a lithium tantalate substrate (first member), a plurality of devices formed on the front side of the substrate, and a plurality of bonding pads (second member) provided on each device and that the plural laser processed holes respectively extend from the back side of the lithium tantalate substrate (first member) to the plural bonding pads (second member), there is no possibility that each bonding pad (second member) may be melted to be perforated.

The above and other objects, features and advantages of the present invention and the manner of realizing them will become more apparent, and the invention itself will best be understood from a study of the following description and appended claim with reference to the attached drawings showing some preferred embodiment of the invention.

DETAILED DESCRIPTION OF THE PREFERRED EMBODIMENT

Figure 1:
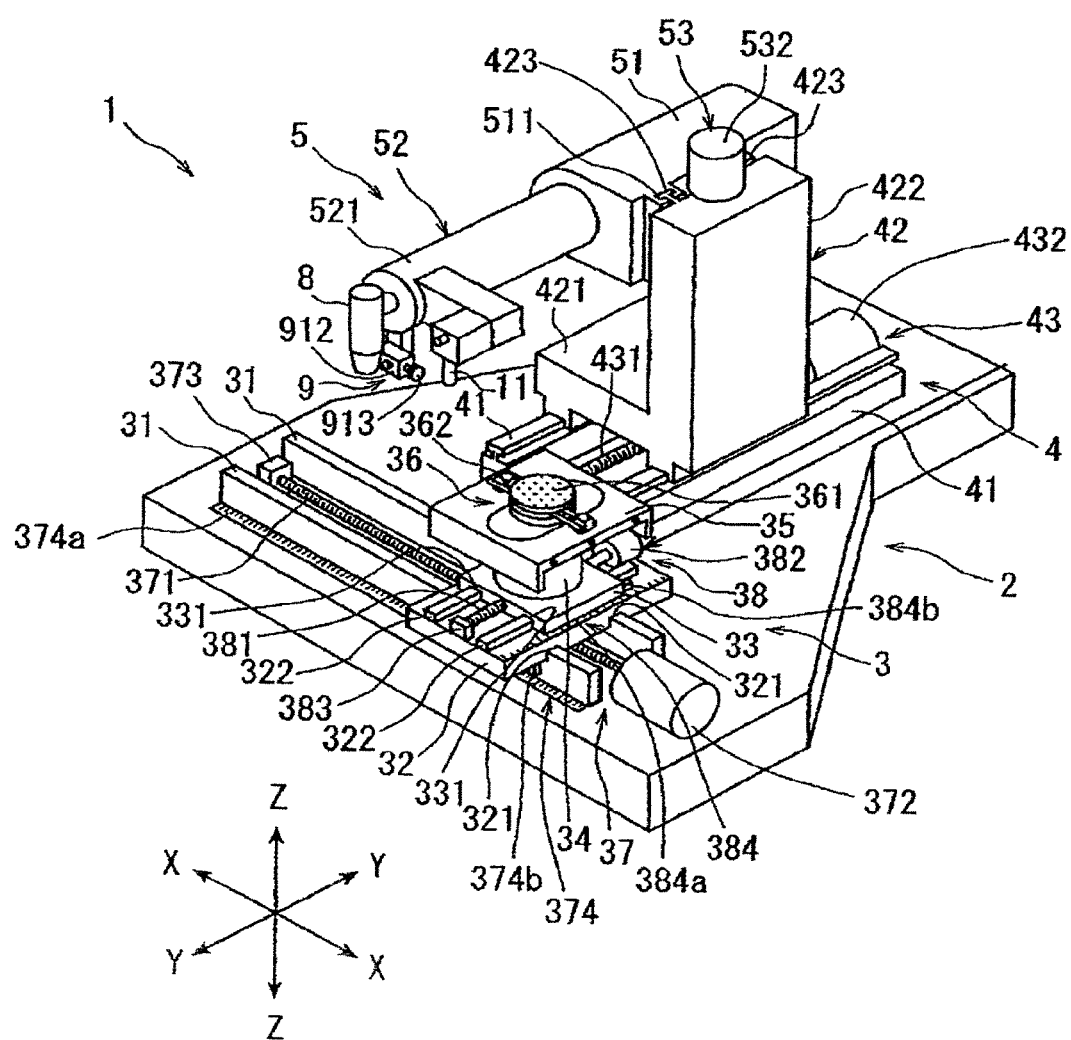
FIG. 1 is a perspective view of a laser processing apparatus according to a preferred embodiment of the present invention.

A preferred embodiment of a laser processing apparatus according to the present invention will now be described in detail with reference to the attached drawings. FIG. 1 is a perspective view of a laser processing apparatus 1 according to the present invention. The laser processing apparatus 1 shown in FIG. 1 includes a stationary base 2, a chuck table mechanism 3 for holding a workpiece, the chuck table mechanism 3 being provided on the stationary base 2 so as to be movable in a feeding direction (X direction) shown by an arrow X, a laser beam applying unit supporting mechanism 4 provided on the stationary base 2 so as to be movable in an indexing direction (Y direction) shown by an arrow Y perpendicular to the X direction, and a laser beam applying unit 5 provided on the laser beam applying unit supporting mechanism 4 so as to be movable in a focal position adjusting direction (Z direction) shown by an arrow Z.

The chuck table mechanism 3 includes a pair of guide rails 31 provided on the stationary base 2 so as to extend parallel to each other in the X direction, a first slide block 32 provided on the guide rails 31 so as to be movable in the X direction, a second slide block 33 provided on the first slide block 32 so as to be movable in the Y direction, a cover table 35 supported by a cylindrical member 34 standing on the second slide block 33, and a chuck table 36 as workpiece holding means. The chuck table 36 has a vacuum chuck 361 formed of a porous material. A workpiece such as a disk-shaped semiconductor wafer is adapted to be held under suction on the vacuum chuck 361 by operating suction means (not shown). The chuck table 36 is rotatable by a pulse motor (not shown) provided in the cylindrical member 34. Further, the chuck table 36 is provided with a clamp 362 for fixing an annular frame to be hereinafter described.

A lower surface of the first slide block 32 is formed with a pair of guided grooves 321 for slidably engaging the pair of guide rails 31 mentioned above. A pair of guide rails 322 is provided on an upper surface of the first slide block 32 so as to extend parallel to each other in the Y direction. Accordingly, the first slide block 32 is movable in the X direction along the guide rails 31 by the slidable engagement of the guided grooves 321 with the guide rails 31. The chuck table mechanism 3 in the shown embodiment further includes feeding means 37 (X direction moving means) for moving the first slide block 32 in the X direction along the guide rails 31. The feeding means 37 includes an externally threaded rod 371 extending parallel to the guide rails 31 so as to be interposed therebetween and a pulse motor 372 as a drive source for rotationally driving the externally threaded rod 371. The externally threaded rod 371 is rotatably supported at one end thereof to a bearing block 373 fixed to the stationary base 2 and is connected at the other end to an output shaft of the pulse motor 372 so as to receive the torque thereof. The externally threaded rod 371 is engaged with a tapped through hole formed in an internally threaded block (not shown) projecting from the lower surface of the first slide block 32 at a central portion thereof. Accordingly, the first slide block 32 is moved in the X direction along the guide rails 31 by operating the pulse motor 372 to normally or reversely rotate the externally threaded rod 371.

The laser processing apparatus 1 includes X position detecting means 374 for detecting the feed amount, or X position of the chuck table 36. The X position detecting means 374 includes a linear scale 374a extending along one of the guide rails 31 and a read head 374b provided on the first slide block 32 and movable along the linear scale 374a together with the first slide block 32. The read head 374b of the X position detecting means 374 transmits a pulse signal of one pulse every 1 μm in this preferred embodiment to control means which will be hereinafter described. This control means counts the number of pulses as the pulse signal input from the read head 374b to thereby detect the feed amount, or X position of the chuck table 36. In the case that the pulse motor 372 is used as the drive source for the feeding means 37 as in this preferred embodiment, the number of pulses as a drive signal output from the control means to the pulse motor 372 may be counted by the control means to thereby detect the feed amount, or X position of the chuck table 36. In a case that a servo motor is used as the drive source for the feeding means 37, a pulse signal output from a rotary encoder for detecting the rotational speed of the servo motor may be sent to the control means, and the number of pulses as the pulse signal input from the rotary encoder into the control means may be counted by the control means to thereby detect the feed amount, or X position of the chuck table 36.

A lower surface of the second slide block 33 is formed with a pair of guided grooves 331 for slidably engaging the pair of guide rails 322 provided on the upper surface of the first slide block 32 as mentioned above. Accordingly, the second slide block 33 is movable in the Y direction along the guide rails 322 by the slidable engagement of the guided grooves 331 with the guide rails 322. The chuck table mechanism 3 in the shown embodiment further includes first indexing means 38 (first Y direction moving means) for moving the second slide block 33 in the Y direction along the guide rails 322 provided on the first slide block 32. The first indexing means 38 includes an externally threaded rod 381 extending parallel to the guide rails 322 so as to be interposed therebetween and a pulse motor 382 as a drive source for rotationally driving the externally threaded rod 381. The externally threaded rod 381 is rotatably supported at one end thereof to a bearing block 383 fixed to the upper surface of the first slide block 32 and is connected at the other end to an output shaft of the pulse motor 382 so as to receive the torque thereof. The externally threaded rod 381 is engaged with a tapped through hole formed in an internally threaded block (not shown) projecting from the lower surface of the second slide block 33 at a central portion thereof. Accordingly, the second slide block 33 is moved in the Y direction along the guide rails 322 by operating the pulse motor 382 to normally or reversely rotate the externally threaded rod 381.

The laser processing apparatus 1 includes Y position detecting means 384 for detecting the index amount, or Y position of the chuck table 36. The Y position detecting means 384 includes a linear scale 384a extending along one of the guide rails 322 and a read head 384b provided on the second slide block 33 and movable along the linear scale 384a together with the second slide block 33. The read head 384b of the Y position detecting means 384 transmits a pulse signal of one pulse every 1 μm in this preferred embodiment to the control means which will be hereinafter described. This control means counts the number of pulses as the pulse signal input from the read head 384b to thereby detect the index amount, or Y position of the chuck table 36. In the case that the pulse motor 382 is used as the drive source for the first indexing means 38 described above, the number of pulses as a drive signal output from the control means to the pulse motor 382 may be counted to thereby detect the index amount, or Y position of the chuck table 36. In a case that a servo motor is used as the drive source for the first indexing means 38, a pulse signal output from a rotary encoder for detecting the rotational speed of the servo motor may be sent to the control means, and the number of pulses as the pulse signal input from the rotary encoder into the control means may be counted by the control means to thereby detect the index amount, or Y position of the chuck table 36.

The laser beam applying unit supporting mechanism 4 includes a pair of guide rails 41 provided on the stationary base 2 so as to extend parallel to each other in the Y direction and a movable support base 42 provided on the guide rails 41 so as to be movable in the Y direction. The movable support base 42 is composed of a horizontal portion 421 slidably supported to the guide rails 41 and a vertical portion 422 extending vertically upward from an upper surface of the horizontal portion 421. Further, a pair of guide rails 423 is provided on one side surface of the vertical portion 422 so as to extend parallel to each other in the Z direction. The laser beam applying unit supporting mechanism 4 in the shown embodiment further includes second indexing means 43 (second Y direction moving means) for moving the movable support base 42 in the Y direction along the guide rails 41. The second indexing means 43 includes an externally threaded rod 431 extending parallel to the guide rails 41 so as to be interposed therebetween and a pulse motor 432 as a drive source for rotationally driving the externally threaded rod 431. The externally threaded rod 431 is rotatably supported at one end thereof to a bearing block (not shown) fixed to the stationary base 2 and is connected at the other end to an output shaft of the pulse motor 432 so as to receive the torque thereof. The externally threaded rod 431 is engaged with a tapped through hole formed in an internally threaded block (not shown) projecting from a lower surface of the horizontal portion 421 at a central portion thereof. Accordingly, the movable support base 42 is moved in the Y direction along the guide rails 41 by operating the pulse motor 432 to normally or reversely rotate the externally threaded rod 431.

The laser beam applying unit 5 includes a unit holder 51 and laser beam applying means 52 mounted to the unit holder 51. The unit holder 51 is formed with a pair of guided grooves 511 for slidably engaging the pair of guide rails 423 provided on the vertical portion 422 of the movable support base 42. Accordingly, the unit holder 51 is supported to the movable support base 42 so as to be movable in the Z direction by the slidable engagement of the guided grooves 511 with the guide rails 423.

The laser beam applying unit 5 further includes focal position adjusting means 53 (Z direction moving means) for moving the unit holder 51 along the guide rails 423 in the Z direction. The focal position adjusting means 53 includes an externally threaded rod (not shown) extending parallel to the guide rails 423 so as to be interposed therebetween and a pulse motor 532 as a drive source for rotationally driving this externally threaded rod. Accordingly, the unit holder 51 and the laser beam applying means 52 are moved in the Z direction along the guide rails 423 by operating the pulse motor 532 to normally or reversely rotate this externally threaded rod. In this preferred embodiment, when the pulse motor 532 is normally operated, the laser beam applying means 52 is moved upward, whereas when the pulse motor 532 is reversely operated, the laser beam applying means 52 is moved downward.

Figure 2:
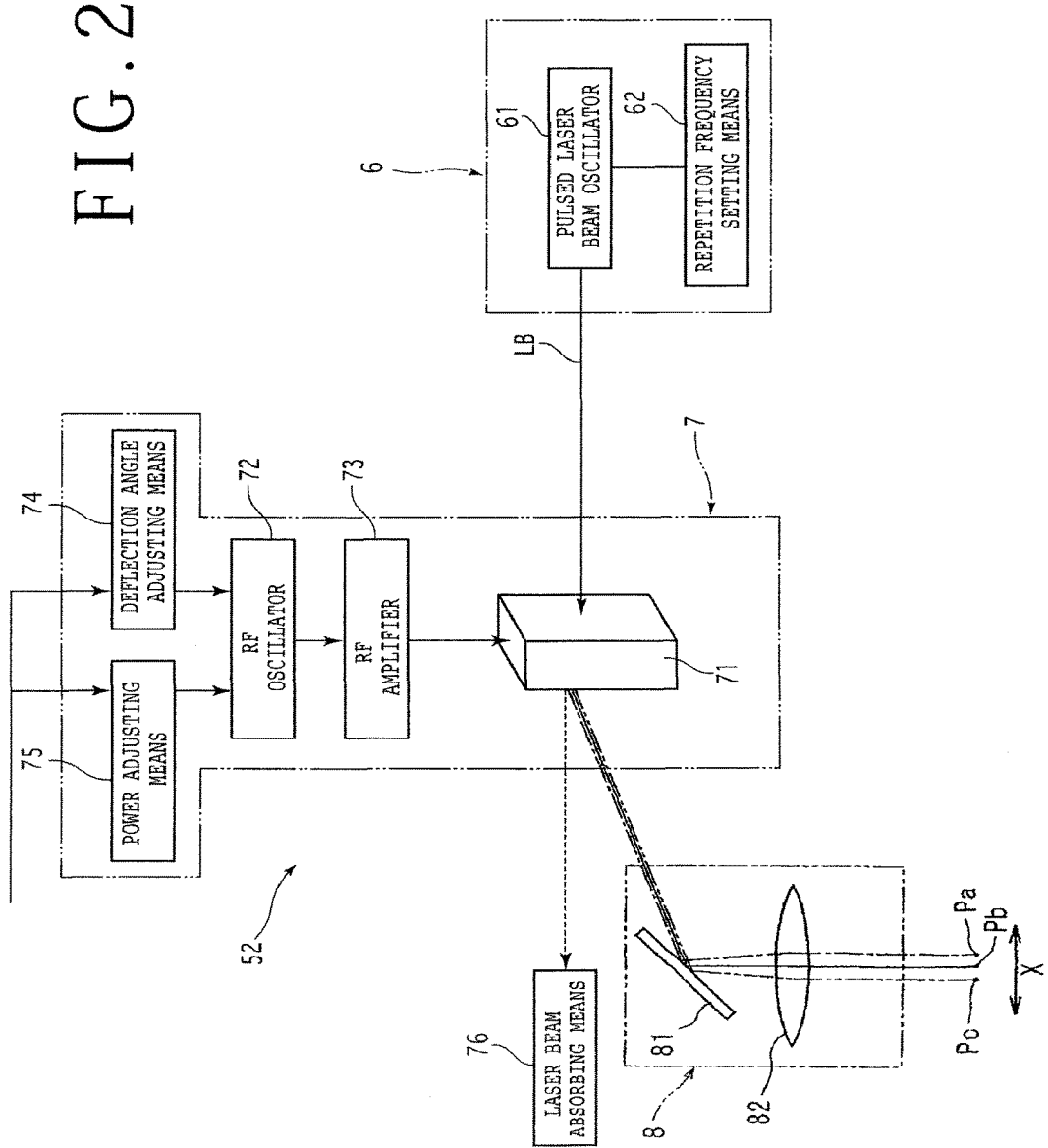
FIG. 2 is a block diagram showing a configuration of laser beam applying means included in the laser processing apparatus shown in FIG. 1.

The laser beam applying means 52 includes a cylindrical casing 521 disposed so as to extend in a substantially horizontal direction, pulsed laser beam oscillating means 6 (see FIG. 2) provided in the casing 521, acoustooptic deflecting means 7 (see FIG. 2) as light deflecting means for deflecting a beam axis of a laser beam oscillated by the pulsed laser beam oscillating means 6 in the feeding direction (X direction), and focusing means 8 (see FIGS. 1 and 2)

for applying the pulsed laser beam passed through the acoustooptic deflecting means 7 to a workpiece W held on the chuck table 36.

The pulsed laser beam oscillating means 6 is composed of a pulsed laser beam oscillator 61 such as a YAG laser oscillator or a YVO4 laser oscillator and repetition frequency setting means 62 connected to the pulsed laser beam oscillator 61. The pulsed laser beam oscillator 61 functions to oscillate a pulsed laser beam (LB) having a predetermined frequency set by the repetition frequency setting means 62. The repetition frequency setting means 62 functions to set the repetition frequency of the pulsed laser beam to be oscillated by the pulsed laser beam oscillator 61.

The acoustooptic deflecting means 7 includes an acoustooptic device 71 for deflecting the beam axis of the pulsed laser beam (LB) oscillated by the pulsed laser beam oscillating means 6, an RF oscillator 72 for generating an RF (radio frequency) signal to be applied to the acoustooptic device 71, an RF amplifier 73 for amplifying the power of the RF signal generated by the RF oscillator 72 and applying the amplified RF signal to the acoustooptic device 71, deflection angle adjusting means 74 for adjusting the frequency of the RF signal to be generated by the RF oscillator 72, and power adjusting means 75 for adjusting the amplitude of the RF signal to be generated by the RF oscillator 72. The acoustooptic device 71 can adjust the angle of deflection of the beam axis of the pulsed laser beam according to the frequency of the RF signal applied and can also adjust the power of the pulsed laser beam according to the amplitude of the RF signal applied. The acoustooptic deflecting means 7 as the light deflecting means may be replaced by electrooptic deflecting means using an electrooptic device. The deflection angle adjusting means 74 and the power adjusting means 75 are controlled by the control means to be described later.

The laser beam applying means 52 further includes laser beam absorbing means 76 for absorbing the pulsed laser beam deflected by the acoustooptic device 71 as shown by a broken line in FIG. 2 in the case that an RF signal having a predetermined frequency is applied to the acoustooptic device 71. The focusing means 8 is mounted at a front end of the casing 521 and it includes a direction changing mirror 81 for downwardly changing the traveling direction of the pulsed laser beam deflected by the acoustooptic deflecting means 7 and a focusing lens 82 provided by a telecentric lens for focusing the pulsed laser beam whose traveling direction has been changed by the direction changing mirror 81.

The laser beam applying means 52 is configured in the above described manner and its operation will now be described with reference to FIG. 2. In a case that a voltage of 5 V, for example, is applied from the control means to the deflection angle adjusting means 74 of the acoustooptic deflecting means 7 and an RF signal having a frequency corresponding to 5 V is applied to the acoustooptic device 71, the pulsed laser beam oscillated by the pulsed laser beam oscillating means 6 is deflected in beam axis as shown by a single dot and dash line in FIG. 2 and focused at a focal point Pa. In a case that a voltage of 10 V, for example, is applied from the control means to the deflection angle adjusting means 74 and an RF signal having a frequency corresponding to 10 V is applied to the acoustooptic device 71, the pulsed laser beam oscillated by the pulsed laser beam oscillating means 6 is deflected in beam axis as shown by a solid line in FIG. 2 and focused at a focal point Pb displaced from the focal point Pa to the left as viewed in FIG. 2 in the feeding direction (X direction) by a predetermined amount. In a case that a voltage of 15 V, for example, is applied from the control means to the deflection angle adjusting means 74 and an RF signal having a frequency corresponding to 15 V is applied to the acoustooptic device 71, the pulsed laser beam oscillated by the pulsed laser beam oscillating means 6 is deflected in beam axis as shown by a double dot and dash line in FIG. 2 and focused at a focal point Pc displaced from the focal point Pb to the left as viewed in FIG. 2 in the X direction by a predetermined amount. Further, in a case that a voltage of 0 V, for example, is applied from the control means to the deflection angle adjusting means 74 and an RF signal having a frequency corresponding to 0 V is applied to the acoustooptic device 71, the pulsed laser beam oscillated by the pulsed laser beam oscillating means 6 is led to the laser beam absorbing means 76 as shown by the broken line in FIG. 2. Thus, the pulsed laser beam is deflected in the X direction by the acoustooptic device 71 according to the voltage applied to the deflection angle adjusting means 74.

Figure 3:
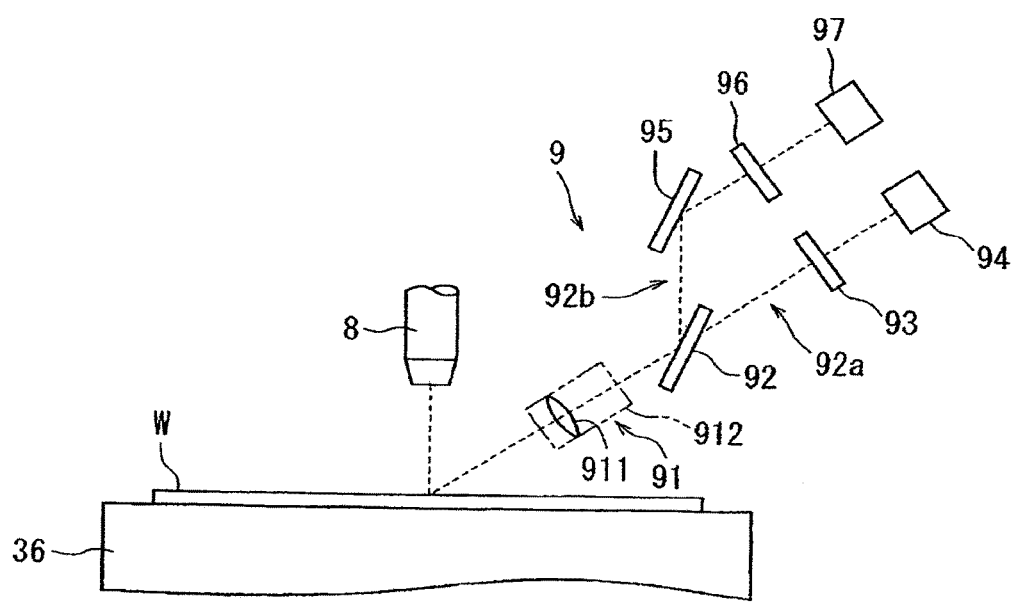
FIG. 3 is a block diagram showing a configuration of plasma detecting means included in the laser processing apparatus shown in FIG. 1.

Referring back to FIG. 1, the laser processing apparatus 1 further includes plasma detecting means 9 mounted on the casing 521 of the laser beam applying means 52 constituting the laser beam applying unit 5 for detecting plasma light generated by applying the laser beam from the laser beam applying means 52 to the workpiece W. As shown in FIG. 3, the plasma detecting means 9 includes plasma capturing means 91 for capturing plasma light generated by applying the laser beam from the focusing means 8 of the laser beam applying means 52 to the workpiece W held on the chuck table 36, a dichroic mirror 92 for separating the plasma light captured by the plasma capturing means 91 into a first optical path 92a and a second optical path 92b, a first bandpass filter 93 provided on the first optical path 92a for passing only the light having a first set wavelength (the wavelength to be generated from a first material forming a first member of the workpiece W to be hereinafter described), a first photodetector 94 for detecting the light passed through the first bandpass filter 93 to output a light intensity signal, a direction changing mirror 95 provided on the second optical path 92b, a second bandpass filter 96 for passing only the light having a second set wavelength (the wavelength to be generated from a second material forming a second member of the workpiece W to be hereinafter described) after the light (plasma light) being reflected on the direction changing mirror 95, and a second photodetector 97 for detecting the light passed through the second bandpass filter 96 to output a light intensity signal.

The plasma capturing means 91 is composed of a focusing lens 911 and a lens case 912 for accommodating the focusing lens 911. As shown in FIG. 1, the lens case 912 is mounted on the casing 521 of the laser beam applying means 52. Further, as shown in FIG. 1, the lens case 912 is provided with an angle adjusting knob 913 for adjusting the installation angle of the focusing lens 911. In the shown embodiment, the first bandpass filter 93 is so configured as to pass the light having a wavelength range of 660 to 680 nm because only the wavelength (670 nm) of plasma light to be generated from lithium tantalate is to be passed. On the other hand, the second bandpass filter 96 is so configured as to pass the light having a wavelength range of 500 to 540 nm because only the wavelength (515 nm) of plasma light to be generated from copper is to be passed. The first photodetector 94 detects the light passed through the first bandpass filter 93 and outputs to the control means a voltage signal corresponding to the intensity of the light detected. Similarly, the second photodetector 97 detects the light passed through the second bandpass filter 96 and outputs to the control means a voltage signal corresponding to the intensity of the light detected. While the plasma detecting means 9 in this preferred embodiment uses the dichroic mirror 92 to separate the plasma light captured by the plasma capturing means 91 into the first optical path 92a and the second optical path 92b, the dichroic mirror 92 may be replaced by a beam splitter.

Referring back to FIG. 1, the laser processing apparatus 1 further includes imaging means 11 provided at a front end portion of the casing 521 for imaging a subject area to be laser-processed by the laser beam applying means 52. The imaging means 11 includes an ordinary imaging device (CCD) for imaging by using visible light, infrared light applying means for applying infrared light to the workpiece W, an optical system for capturing the infrared light applied by the infrared light applying means, and an imaging device (infrared CCD) for outputting an electrical signal corresponding to the infrared light captured by the optical system. An image signal output from the imaging means 11 is transmitted to the control means described below.

Figure 4:
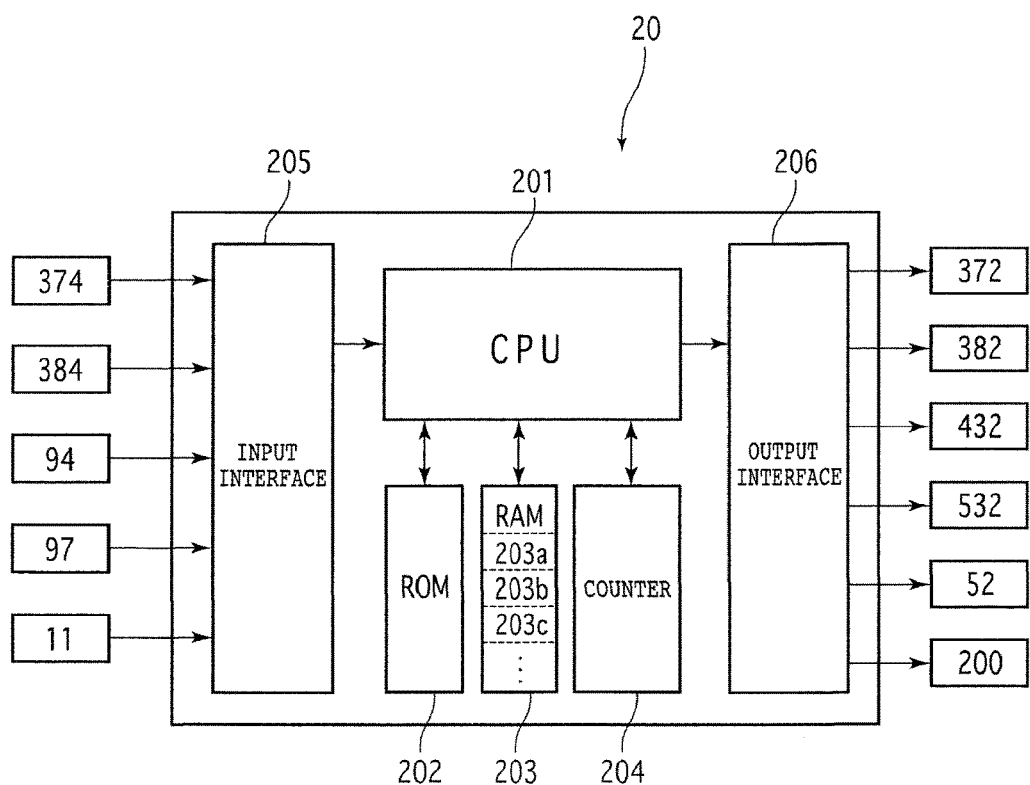
FIG. 4 is a block diagram showing a configuration of control means included in the laser processing apparatus shown in FIG. 1.

The laser processing apparatus 1 includes the control means 20 shown in FIG. 4. The control means 20 is configured by a computer, and it includes a central processing unit (CPU) 201 for performing operational processing according to a control program, a read only memory (ROM) 202 storing the control program and the like, a readable and writable random access memory (RAM) 203 for storing a control map to be described later, data on design value for the workpiece W, the results of computation, etc., a counter 204, an input interface 205, and an output interface 206. Detection signals from the X position detecting means 374, the Y position detecting means 384, the first and second photodetectors 94 and 97 of the plasma detecting means 9, and the imaging means 11 are input into the input interface 205 of the control means 20. On the other hand, control signals are output from the output interface 206 of the control means 20 to the pulse motor 372, the pulse motor 382, the pulse motor 432, the pulse motor 532, the laser beam applying means 52, and display means 200. The random access memory (RAM) 203 includes a first memory area 203a for storing a relation between the material of the workpiece W and the wavelength of plasma light, a second memory area 203b for storing data on design value for a wafer to be hereinafter described, a third memory area 203c for storing a predetermined value for the amplitude of a light intensity to be hereinafter described, and other memory areas.

Figure 5:
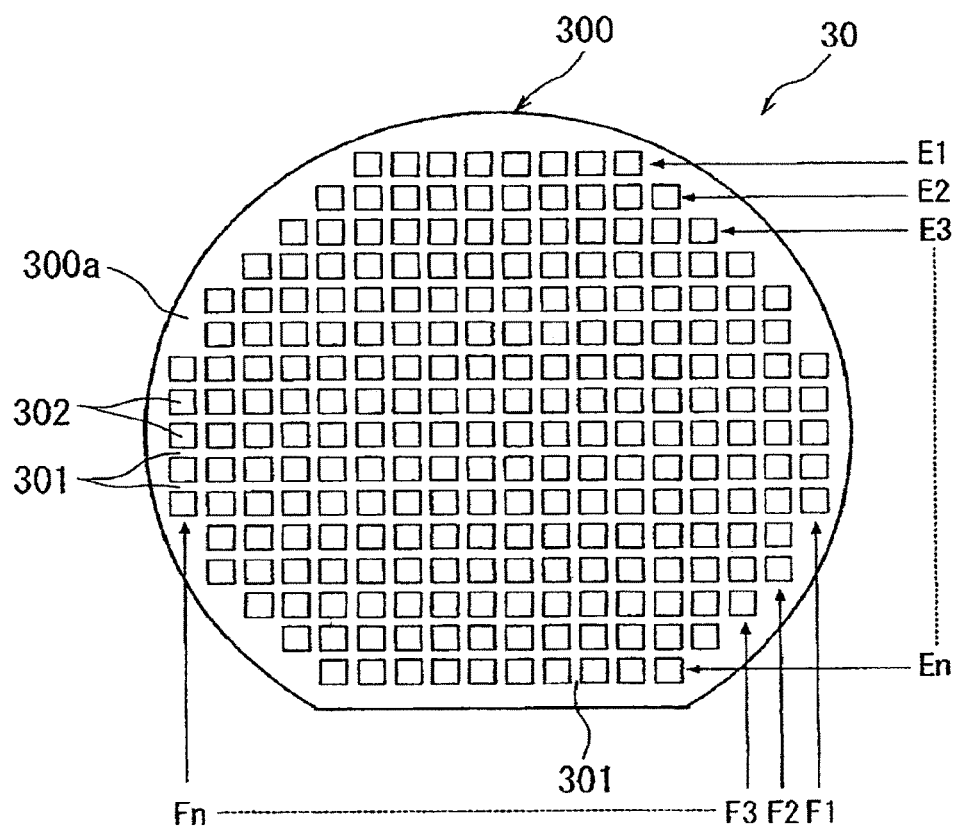
FIG. 5 is a plan view of a semiconductor wafer as a workpiece.
Figure 6:
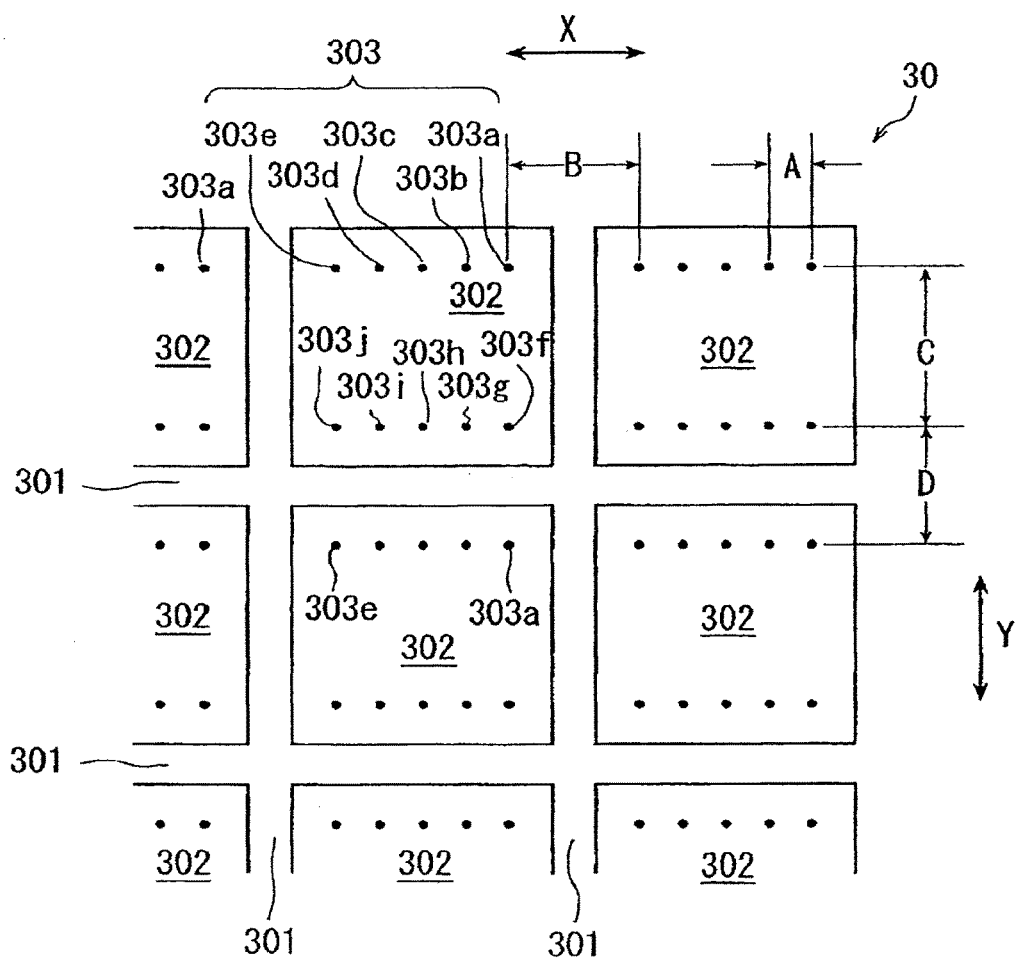
FIG. 6 is an enlarged plan view of part of the semiconductor wafer shown in FIG. 5.

The operation of the laser processing apparatus 1 configured above will now be described. FIG. 5 is a plan view of a wafer 30 as the workpiece W to be laser-processed. The wafer 30 in the preferred embodiment shown in FIG. 5 is formed from a lithium tantalate substrate 300 (first member) having a thickness of 300 μm, for example. A plurality of crossing division lines 301 are formed on a front side 300a of the substrate 300, thereby partitioning a plurality of rectangular regions where a plurality of devices 302 are respectively formed. All of the devices 302 have the same configuration. As shown in FIG. 6, a plurality of bonding pads 303 (303a to 303j) (second member) are formed on a front side of each device 302. In this preferred embodiment, these bonding pads 303 (303a to 303j) as the second member are formed of copper. The bonding pads 303a and 303f have the same X position, the bonding pads 303b and 303g have the same X position, the bonding pads 303c and 303h have the same X position, the bonding pads 303d and 303i have the same X position, and the bonding pads 303e and 303j have the same X position. A processed hole (via hole) is formed so as to extend from a back side 300b of the substrate 300 to each of the bonding pads 303 (303a to 303j). In each device 302, the bonding pads 303 (303a to 303j) are equally spaced at given intervals A in the X direction (horizontal direction as viewed in FIG. 6). More specifically, the spacing A between the bonding pads 303a and 303b is equal to the spacing between the bonding pads 303b and 303c, the spacing between the bonding pads 303c and 303d, the spacing between the bonding pads 303d and 303e, the spacing between the bonding pads 303f and 303g, the spacing between the bonding pads 303g and 303h, the spacing between the bonding pads 303h and 303i, and the spacing between the bonding pads 303i and 303j. Further, in the adjacent devices 302 opposed in the X direction with respect to a vertical division line 301, the adjacent bonding pads 303 are equally spaced at given intervals B in the X direction. More specifically, the spacing B between the bonding pads 303e and 303a in the adjacent devices 302 in the X direction is equal to the spacing between the bonding pads 303j and 303f in the adjacent devices 302 in the X direction. Further, in each device 302, the bonding pads 303 (303a to 303j) are equally spaced at given intervals C in the Y direction (vertical direction as viewed in FIG. 6). More specifically, the spacing C between the bonding pads 303a and 303f is equal to the spacing between the bonding pads 303b and 303g, the spacing between the bonding pads 303c and 303h, the spacing between the bonding pads 303d and 303i, and the spacing between the bonding pads 303e and 303j. Further, in the adjacent devices 302 opposed in the Y direction with respect to a horizontal division line 301, the adjacent bonding pads 303 are equally spaced at given intervals D in the Y direction. More specifically, the spacing D between the bonding pads 303f and 303a in the adjacent devices 302 in the Y direction is equal to the spacing between the bonding pads 303g and 303b in the adjacent devices 302 in the Y direction, the spacing between the bonding pads 303h and 303c in the adjacent devices 302 in the Y direction, the spacing between the bonding pads 303i and 303d in the adjacent devices 302 in the Y direction, and the spacing between the bonding pads 303j and 303e in the adjacent devices 302 in the Y direction. As for the wafer 30 configured in the above described manner, referring to FIG. 5, symbols E1 to En denote the rows of the devices 302 and symbols F1 to Fn denote the columns of the devices 302. Data on design value for the number of devices 302 in each of the rows E1 to En and the columns F1 to Fn, the values of the spacings A, B, C, and D mentioned above, and the X and Y coordinate values are stored in the second memory area 203b of the random access memory (RAM) 203.

Figure 7:
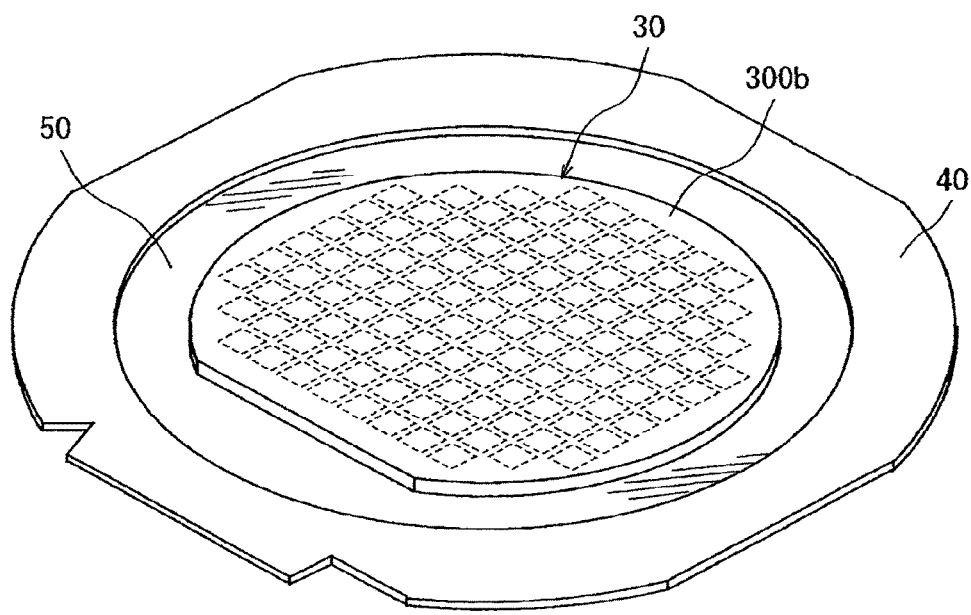
FIG. 7 is a perspective view showing a condition where the semiconductor wafer shown in FIG. 5 is attached to a protective tape supported to an annular frame.

There will now be described a laser processing operation in the preferred embodiment of processing the wafer 30 by using the laser processing apparatus 1 to form a laser processed hole (via hole) at the portion of each of the bonding pads 303 (303a to 303j) in each device 302. As shown in FIG. 7, the wafer 30 is supported through a protective tape 50 to an annular frame 40 in such a manner that the front side 300a of the substrate 300 constituting the wafer 30 is attached to the protective tape 50 which is preliminarily supported to the annular frame 40. The protective tape 50 is formed from a synthetic resin sheet such as a polyolefin sheet. Accordingly, the back side 300b of the substrate 300 constituting the wafer 30 attached to the protective tape 50 is oriented upward. The wafer 30 supported through the protective tape 50 to the annular frame 40 is placed on the chuck table 36 of the laser processing apparatus 1 shown in FIG. 1 in the condition where the protective tape 50 comes into contact with an upper surface of the chuck table 36. Thereafter, the suction means (not shown) is operated to hold the wafer 30 through the protective tape 50 on the chuck table 36 under suction. Accordingly, the wafer 30 is held on the chuck table 36 in the condition where the back side 300b of the substrate 300 constituting the wafer 30 is oriented upward. Further, the annular frame 40 is fixed by the clamp 362.

Thereafter, the feeding means 37 is operated to move the chuck table 36 holding the wafer 30 under suction to a position directly below the imaging means 11. In the condition where the chuck table 36 is positioned directly below the imaging means 11, the wafer 30 on the chuck table 36 is set at a coordinate position shown in FIG. 8. In this condition, an alignment operation is performed to detect whether or not the crossing division lines 301 of the wafer 30 held on the chuck table 36 are parallel to the X direction and the Y direction. That is, the imaging means 11 is operated to image the wafer 30 held on the chuck table 36 and perform image processing such as pattern matching, thus performing the alignment operation. Although the front side 300a on which the division lines 301 of the wafer 30 are formed is oriented downward, the division lines 301 can be imaged from the back side 300b through the substrate 300 of the wafer 30 because the lithium tantalate substrate 300 constituting the wafer 30 is transparent.

Figure 8:
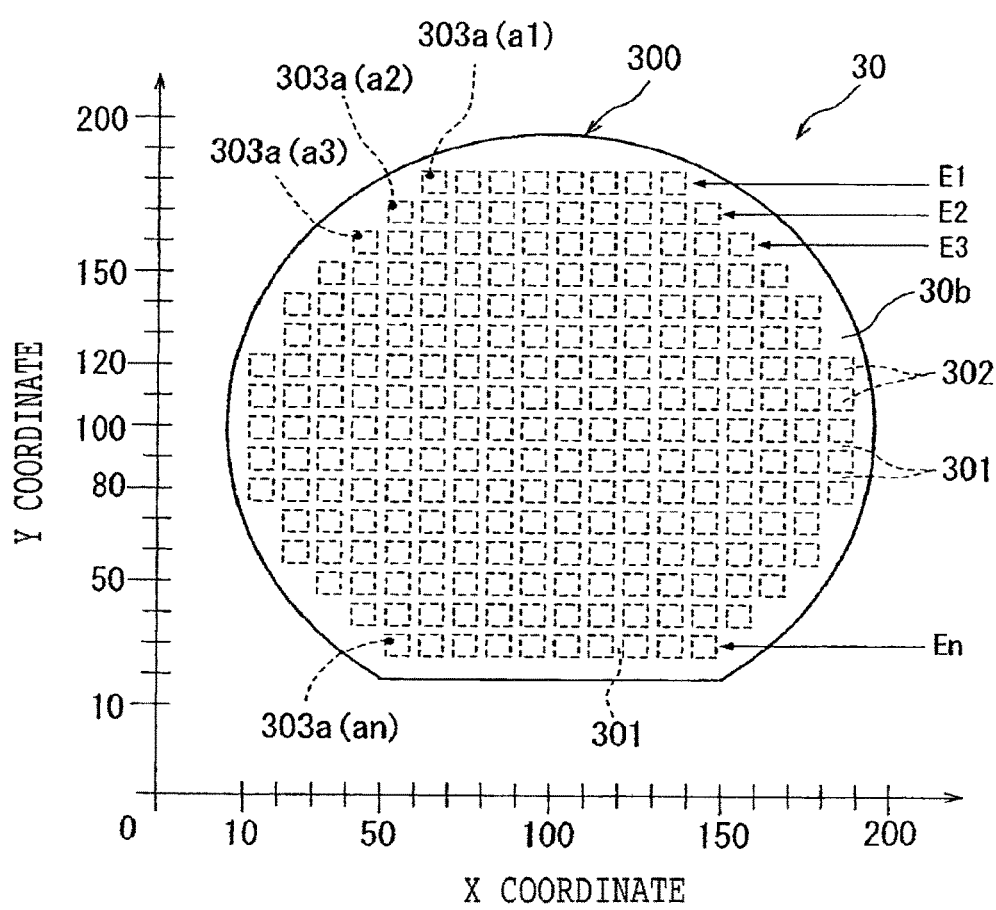
FIG. 8 is a plan view showing a relation between the semiconductor wafer shown in FIG. 5 and coordinates in a condition where the wafer is held at a predetermined position on a chuck table included in the laser processing apparatus shown in FIG. 1.

Thereafter, the chuck table 36 is moved to position the leftmost device 302 on the uppermost row E1 as viewed in FIG. 8 directly below the imaging means 11. Further, a left upper electrode (bonding pad) 303a of electrodes (bonding pads) 303 (303a to 303j) in this leftmost device 302 as viewed in FIG. 8 is positioned directly below the imaging means 11. In this condition, the electrode 303a is detected by the imaging means 11 and a coordinate value (a1) for the electrode 303a is sent as a first feed start position coordinate value to the control means 20. The control means 20 stores this coordinate value (a1) as the first feed start position coordinate value into the random access memory (RAM) 203 (feed start position detecting step). The imaging means 11 and the focusing means 8 of the laser beam applying means 52 are spaced a predetermined distance in the X direction. Accordingly, the sum of the X coordinate value constituting the first feed start position coordinate value and the above predetermined distance between the imaging means 11 and the focusing means 8 is stored into the RAM 203.

After detecting the first feed start position coordinate value (a1) in the leftmost device 302 on the uppermost row E1 as viewed in FIG. 8, the chuck table 36 is moved in the Y direction by the pitch of the division lines 301 and also moved in the X direction to position the leftmost device 302 on the second uppermost row E2 as viewed in FIG. 8 directly below the imaging means 11. Further, the left upper electrode 303a of the electrodes 303 (303a to 303j) in this leftmost device 302 as viewed in FIG. 8 is positioned directly below the imaging means 11. In this condition, the electrode 303a is detected by the imaging means 11 and a coordinate value (a2) for the electrode 303a is sent as a second feed start position coordinate value to the control means 20. The control means 20 stores this coordinate value (a2) as the second feed start position coordinate value into the random access memory (RAM) 203. As mentioned above, the imaging means 11 and the focusing means 8 of the laser beam applying means 52 are spaced a predetermined distance in the X direction. Accordingly, the sum of the X coordinate value constituting the second feed start position coordinate value and the above distance between the imaging means 11 and the focusing means 8 is stored into the RAM 203. Thereafter, the control means 20 repeatedly performs the indexing operation (stepwise movement in the Y direction) and the feed start position detecting step mentioned above until the lowermost row En as viewed in FIG. 8 to detect the feed start position coordinate values (a3 to an) for the leftmost devices 302 on the other rows (E3 to En) and store these coordinate values into the random access memory (RAM) 203.

Figure 9A:
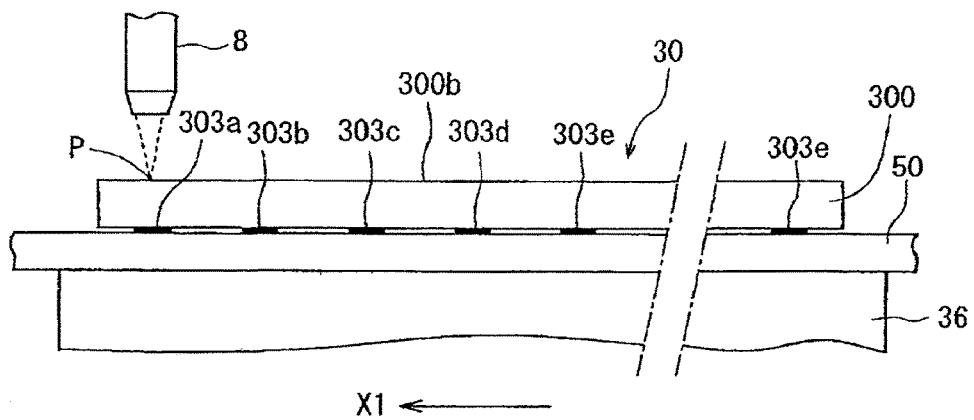
FIGS. 9A and 9B are views for illustrating a hole forming step to be performed by the laser processing apparatus shown in FIG. 1.

After performing the feed start position detecting step mentioned above, a hole forming step is performed to form a laser processed hole (via hole) from the back side of the substrate 300 of the wafer 30 at each of the electrodes 303 (303a to 303j) formed in each device 302. In this hole forming step, the feeding means 37 is first operated to move the chuck table 36 so that the bonding pad 303a corresponding to the first feed start position coordinate value (a1) stored in the random access memory (RAM) 203 is positioned directly below the focusing means 8 of the laser beam applying means 52. FIG. 9A shows this condition where the bonding pad 303a corresponding to the first feed start position coordinate value (a1) is positioned directly below the focusing means 8. Then, the feeding means 37 is controlled by the control means 20 to feed the chuck table 36 at a predetermined feed speed in the direction shown by an arrow X1 in FIG. 9A. At the same time, the laser beam applying means 52 is controlled by the control means 20 to apply a pulsed laser beam from the focusing means 8 to the wafer 30. The focal point P of the pulsed laser beam to be applied from the focusing means 8 is set near the back side 300b (upper surface as viewed in FIG. 9A) of the substrate 300 of the wafer 30. At this time, the control means 20 outputs a control signal for controlling the deflection angle adjusting means 74 and the power adjusting means 75 of the acoustooptic deflecting means 7 according to a detection signal from the read head 374b of the X position detecting means 374.

On the other hand, the RF oscillator 72 outputs an RF signal corresponding to the control signal from the deflection angle adjusting means 74 and the power adjusting means 75. The power of the RF signal output from the RF oscillator 72 is amplified by the RF amplifier 73, and the amplified RF signal is applied to the acoustooptic device 71. As a result, the acoustooptic device 71 deflects the beam axis of the pulsed laser beam oscillated by the pulsed laser beam oscillating means 6 in the range from the position shown by the single dot and dash line in FIG. 2 to the position shown by the double dot and dash line in FIG. 2 in synchronism with the feed speed of the chuck table 36. As a result, the pulsed laser beam having a predetermined power can be applied to the wafer 30 at the position of the bonding pad 303a corresponding to the first feed start position coordinate value (a1).

For example, the hole forming step mentioned above may be performed under the following processing conditions.

Light source: LD pumped Q-switched Nd:YVO4 pulsed laser
Wavelength: 532 nm
Average power: 2 W
Repetition frequency: 50 kHz
Pulse width: 10 ps
Focused spot diameter: φ 15 µm In performing the hole forming step, the control means 20 operates the counter 204 to count the number of shots of the pulsed laser beam oscillated by the pulsed laser beam oscillating means 6 and also operates the plasma detecting means 9 to input a light intensity signal from the first photodetector 94. The light intensity signal to be output from the first photodetector 94 will now be described. When the pulsed laser beam is applied to the lithium tantalate substrate 300 constituting the wafer 30, plasma light having a wavelength of 670 nm is generated. This plasma light having the wavelength of 670 nm is focused by the focusing lens 911 of the plasma capturing means 91 constituting the plasma detecting means 9 as shown in FIG. 3 and then passed through the first bandpass filter 93 to reach the first photodetector 94. When the pulsed laser beam is applied to a transparent member of lithium tantalate, for example, the surface of the transparent member is roughened by a first operation of the pulsed laser beam and the roughened surface of the transparent member is next ablated by a second operation of the pulsed laser beam. Thus, when the pulsed laser beam is applied to a transparent member of lithium tantalate, for example, the roughening and the ablation of the surface of the transparent member are repeatedly performed. At this time, the light intensity of plasma light generated from the transparent member by the ablation is higher than the light intensity of plasma light generated from the transparent member by the roughening. Accordingly, when the pulsed laser beam is applied to a transparent member of lithium tantalate, for example, the light intensity of plasma light varies every time each pulse of the pulsed laser beam is applied.

Figure 11:
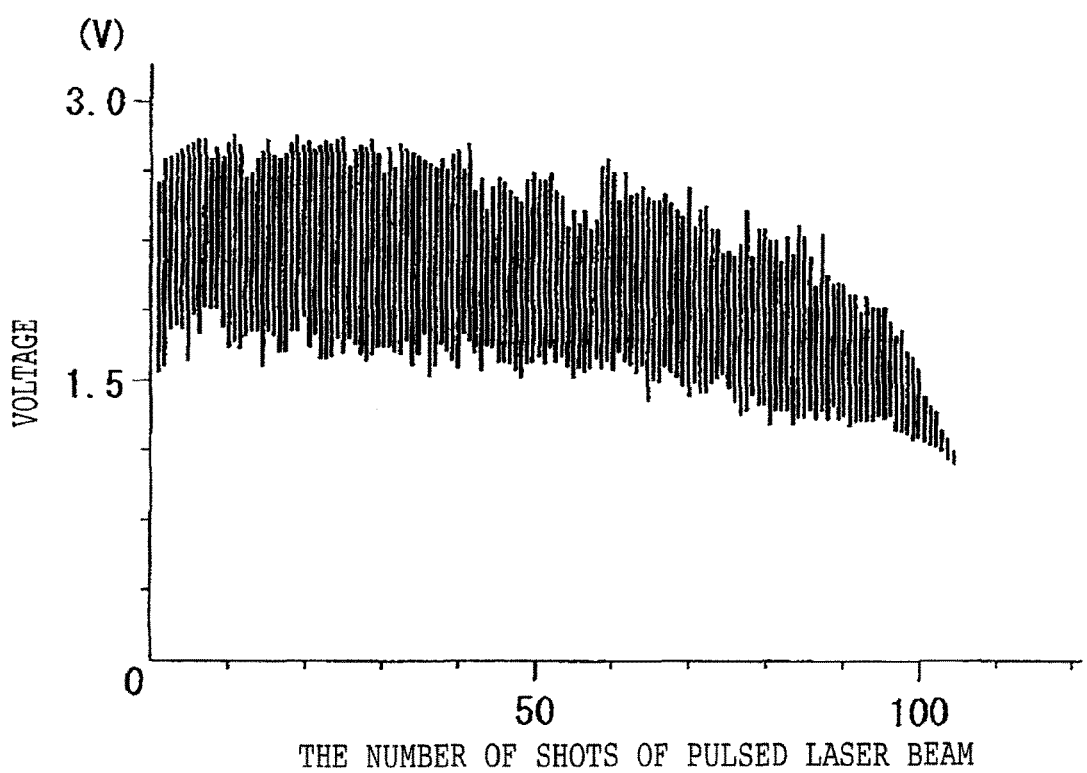
FIG. 11 is a graph showing an output voltage from a photodetector for detecting the light intensity of plasma light generated by applying a pulsed laser beam to a lithium tantalate substrate.

FIG. 11 shows an output voltage from the first photodetector 94 for detecting the light intensity of plasma light generated by applying the pulsed laser beam to the lithium tantalate substrate 300. In FIG. 11, a horizontal axis represents the number of shots of the pulsed laser beam, and a vertical axis represents voltage (V). In the preferred embodiment shown in FIG. 11, a lower limit of voltage in each shot of the pulsed laser beam corresponds to the light intensity of plasma light generated by the first operation of pulsed laser beam to roughen the surface of a transparent member, whereas an upper limit of voltage in each shot of the pulsed laser beam corresponds to the light intensity of plasma light generated by the second operation of pulsed laser beam to ablate the roughened surface of the transparent member. In the preferred embodiment shown in FIG. 11, the output voltage from the first photodetector 94 varies in a range from 1.5 V to 3 V with an amplitude of about 1.1 V until the number of shots of the pulsed laser beam becomes about 60. When the number of shots of the pulsed laser beam exceeds 60, both the upper limit and the lower limit of the output voltage are gradually decreased. When the number of shots of the pulsed laser beam exceeds 90, the amplitude (the range of variations) of the output voltage from the first photodetector 94 is gradually decreased. When the number of shots of the pulsed laser beam exceeds 105, the output voltage from the first photodetector 94 becomes zero, which means that the processing of the lithium tantalate substrate 300 has been finished. That is, if the application of the pulsed laser beam is continued from this time, the bonding pad 303a is undesirably processed by the pulsed laser beam.

Accordingly, the time of stopping the application of the pulsed laser beam can be set by experimentally determining how many shots of the pulsed laser beam should be applied from the time the amplitude of the output voltage from the first photodetector 94 is decreased to a predetermined value (0.1 V) to the time the pulsed laser beam reaches the bonding pad 303a.

There will now be described an example of experimentally determining how many shots of the pulsed laser beam should be applied from the time the amplitude of the output voltage from the first photodetector 94 is decreased to the predetermined value (0.1 V) to the time the pulsed laser beam reaches the bonding pad 303a. As described above, the plasma detecting means 9 includes the second bandpass filter 96 allowing the pass of only the wavelength (515 nm) of plasma light generated from copper in the wavelength range of plasma light guided to the second optical path 92b and also includes the second photodetector 97 for detecting the plasma light passed through the second bandpass filter 96 to output a light intensity signal. Accordingly, the moment of processing of the bonding pad 303a can be captured. By counting the number of shots of the pulsed laser beam applied from the time the amplitude of the output voltage from the first photodetector 94 is decreased to the predetermined value (0.1 V), it is possible to determine the number of shots applied from the time of decrease in amplitude of the output voltage to the predetermined value (0.1 V) to the time of processing of the bonding pad 303a. For example, in a case that the number of shots applied from the time of decrease in amplitude of the output voltage to the predetermined value (0.1 V) to the time of processing of the bonding pad 303a is five, the application of the pulsed later beam is to be stopped after the amplitude of the output voltage from the first photodetector 94 is decreased to the predetermined value (0.1 V) and then five shots of the pulsed laser beam are applied. In other words, when the amplitude of the output voltage from the first photodetector 94 is decreased to the predetermined value (0.1 V) and then five shots of the pulsed laser beam are applied, the control means 20 determines that the pulsed laser beam has reached the bonding pad 303a formed of copper and then applies a voltage of 0 V to the deflection angle adjusting means 74 of the acoustooptic deflecting means 7. Accordingly, an RF signal having a frequency corresponding to 0 V is applied to the acoustooptic device 71, so that the pulsed laser beam oscillated by the pulsed laser beam oscillating means 6 is led to the laser beam absorbing means 76 as shown by the broken line in FIG. 2. Accordingly, the pulsed laser beam is not applied to the wafer 30 held on the chuck table 36, thereby preventing the bonding pad 303a from being melted to be perforated.

Figure 9B:
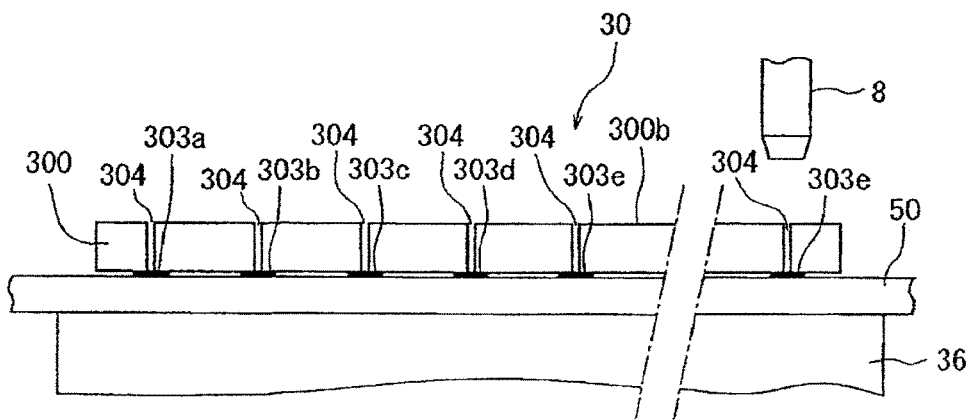

The control means 20 inputs a detection signal from the read head 374b of the X position detecting means 374 and counts this detection signal through the counter 204. When the count value by the counter 204 reaches the coordinate value for the next bonding pad 303b in the X direction, the control means 20 controls the laser beam applying means 52 to similarly perform the hole forming step. Thereafter, every time the count value by the counter 204 reaches the coordinate value for each bonding pad 303 (303c to 303e), the control means 20 operates the laser beam applying means 52 to similarly perform the hole forming step. When the hole forming step is performed at the position of the rightmost electrode 303e in the rightmost device 302 on the uppermost row E1 of the wafer 30 as shown in FIG. 9B, the operation of the feeding means 37 is stopped to stop the movement of the chuck table 36. As a result, a plurality of laser processed holes 304 respectively reaching the bonding pads 303a to 303e in each device 302 on the uppermost row E1 are formed through the lithium tantalate substrate 300 of the wafer 30 as shown in FIG. 9B.

Figure 10A:
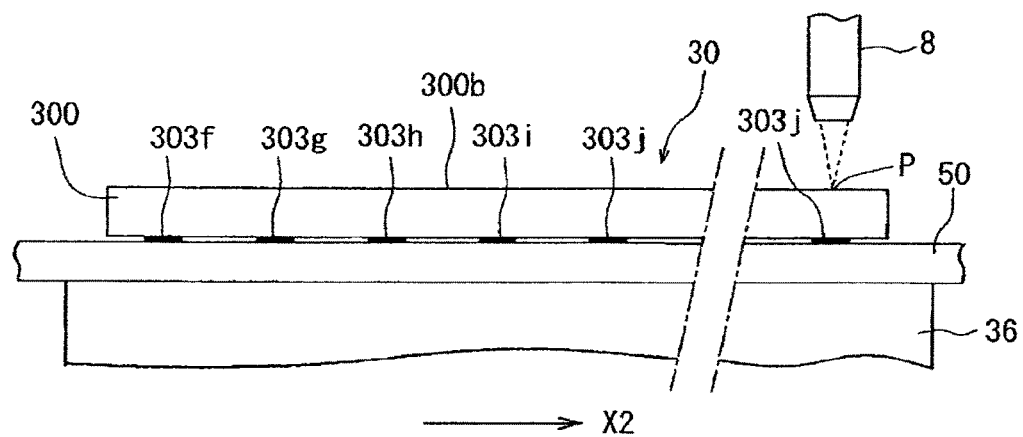
FIGS. 10A and 10B are views similar to FIGS. 9A and 9B, showing the step subsequent to the step shown in FIGS. 9A and 9B.
Figure 10B:
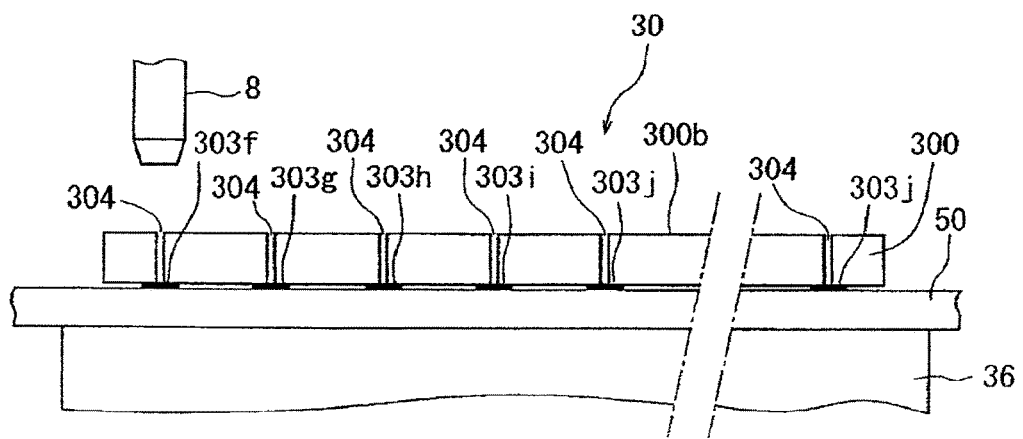

Thereafter, the control means 20 controls the first indexing means 38 to index the focusing means 8 of the laser beam applying means 52 in a direction perpendicular to the sheet plane of FIG. 9B, i.e., in the Y direction. On the other hand, the control means 20 inputs a detection signal from the read head 384b of the Y position detecting means 384 and counts this detection signal through the counter 204. When the count value by the counter 204 reaches a value corresponding to the spacing C of the bonding pads 303 in the Y direction shown in FIG. 6, the operation of the first indexing means 38 is stopped to stop the indexing of the focusing means 8. As a result, the focusing means 8 is positioned directly above the bonding pad 303*j* (see FIG. 6) opposed to the bonding pad 303*e* in the Y direction. FIG. 10A shows this condition where the focusing means 8 is positioned directly above the bonding pad 303*j* in the rightmost device 302 on the uppermost row E1. Thereafter, the control means 20 controls the feeding means 37 to feed the chuck table 36 in a direction shown by an arrow X2 in FIG. 10A at a predetermined feed speed. At the same time, the control means 20 operates the laser beam applying means 52 to perform the hole forming step. As described above, the control means 20 inputs a detection signal from the read head 374*b* of the X position detecting means 374 and counts this detection signal through the counter 204. Every time the count value reaches the coordinate value for each bonding pad 303 (303*j* to 303*f*), the control means 20 operates the laser beam applying means 52 to similarly perform the hole forming step. When the hole forming step is performed at the position of the leftmost bonding pad 303*f* in the leftmost device 302 on the uppermost row E1 of the wafer 30 as shown in FIG. 10B, the operation of the feeding means 37 is stopped to stop the movement of the chuck table 36. As a result, a plurality of laser processed holes 304 respectively reaching the bonding pads 303*j* to 303*f* in each device 302 on the uppermost row E1 are formed through the lithium tantalate substrate 300 of the wafer 30 as shown in FIG. 10B.

Thus, the laser processed holes 304 are formed through the substrate 300 of the wafer 30 on the back side of the bonding pads 303 in each device 302 on the uppermost row E1 as described above. Thereafter, the control means 20 operates the feeding means 37 and the first indexing means 38 to position the bonding pad 303*a* corresponding to the second feed start position coordinate value (a2) directly below the focusing means 8 of the laser beam applying means 52, the bonding pad 303*a* corresponding to the second feed start position coordinate value (a2) being formed in the leftmost device 302 on the second uppermost row E2 of the wafer 30 and being stored in the random access memory (RAM) 203. Thereafter, the control means 20 controls the laser beam applying means 52, the feeding means 37, and the first indexing means 38 to perform the hole forming step on the back side of the bonding pads 303 in the other devices 302 on the second uppermost row E2 of the wafer 30. Thereafter, the hole forming step is similarly performed on the back side of the bonding pads 303 in the devices 302 on the other rows E3 to En of the wafer 30. As a result, a plurality of laser processed holes 304 on the back side of the bonding pads 303 in all the devices 302 on the other rows E3 to En are formed through the lithium tantalate substrate 300 of the wafer 30.

In the hole forming step mentioned above, the pulsed laser beam is not applied to the areas of the wafer 30 corresponding to the spacing A and the spacing B in the X direction and the spacing C and the spacing D in the Y direction shown in FIG. 6. To avoid the application of the pulsed laser beam to these areas corresponding to the spacings A, B, C, and D in the wafer 30, the control means 20 applies a voltage of 0 V to the deflection angle adjusting means 74 of the acoustooptic deflecting means 7. As a result, an RF signal having a frequency corresponding to 0 V is applied to the acoustooptic device 71, so that the pulsed laser beam (LB) oscillated by the pulsed laser beam oscillating means 6 is led to the laser beam absorbing means 76 as shown by the broken line in FIG. 2, thereby avoiding the application of the pulsed laser beam to the wafer 30.

While a specific preferred embodiment of the present invention has been described, it should be noted that the present invention is not limited to the above preferred embodiment, but various modifications may be made within the scope of the present invention. For example, in the above preferred embodiment, the plural laser processed holes are formed in the wafer including the substrate (first member), the plural devices formed on the front side of the substrate, and the plural bonding pads (second member) provided on each device, the plural laser processed holes respectively extending from the back side of the substrate (first member) to the plural bonding pads (second member). However, the present invention is widely applicable to the case of forming a laser processed hole in a workpiece configured by bonding a first member formed of a first material and a second member formed of a second material, the laser processed hole extending from the first member to the second member. Further, while a lithium tantalate substrate is used as the first member forming the workpiece in this preferred embodiment, the present invention is effective especially for processing of a transparent member formed of lithium niobate, sapphire, quartz, etc.

The present invention is not limited to the details of the above described preferred embodiment. The scope of the invention is defined by the appended claim and all changes and modifications as fall within the equivalence of the scope of the claim are therefore to be embraced by the invention.

What is claimed is:

1. A method for forming a laser processed hole in a workpiece configured by bonding a transparent first member formed of a first material and a second member formed of a second material, the laser processed hole extending from the first member to the second member, the method comprising:
   holding the workpiece by a chuck table with a side of the first member directed upward;
   applying a pulsed laser beam to the workpiece from the upward side of the first member;
   detecting a wavelength of plasma light generated by applying the pulsed laser beam to the workpiece; and
   controlling the laser beam according to a detection signal from the plasma light,
   wherein the plasma is detected by:
   passing only the wavelength of plasma light generated from the first material, and
   detecting the plasma light generated from the first material and outputting a light intensity signal based on the detection, the light intensity of the plasma light being varied every time each pulse of the pulsed laser beam is applied;
   wherein shots of the pulsed laser beam are applied to the workpiece to thereby form the laser processed hole extending from the first member to the second member by monitoring the amplitude of the light intensity and stopping the pulsed laser beam after the amplitude of the light intensity is decreased to a predetermined value and a predetermined number of additional shots of the pulsed laser beam have been applied,
   whereby the processed hole extends entirely through the first member without melting the second member.

* * * * *